United States Patent
Green et al.

(10) Patent No.: US 10,064,804 B2
(45) Date of Patent: Sep. 4, 2018

(54) POLYMERIC NITRONES AND THEIR USE IN PERSONAL CARE

(71) Applicant: Dow Global Technologies LLC, Midland, MI (US)

(72) Inventors: George D. Green, Cary, IL (US); Raymond J. Swedo, Mount Prospect, IL (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 15/318,863

(22) PCT Filed: Jun. 25, 2015

(86) PCT No.: PCT/US2015/037710
§ 371 (c)(1),
(2) Date: Dec. 14, 2016

(87) PCT Pub. No.: WO2016/003767
PCT Pub. Date: Jan. 7, 2016

(65) Prior Publication Data
US 2017/0135941 A1    May 18, 2017

Related U.S. Application Data

(60) Provisional application No. 62/018,910, filed on Jun. 30, 2014.

(51) Int. Cl.
*A61K 8/81* (2006.01)
*A61K 31/15* (2006.01)
(Continued)

(52) U.S. Cl.
CPC .......... *A61K 8/8152* (2013.01); *A61K 9/0014* (2013.01); *A61K 31/15* (2013.01);
(Continued)

(58) Field of Classification Search
CPC .. A61K 2800/522; A61K 31/15; A61Q 19/08; C08F 226/02; C08L 33/14; C09D 133/14
See application file for complete search history.

(56) References Cited

U.S. PATENT DOCUMENTS 5,176,983 A * 1/1993 Horn ............... C08F 220/36
430/270.1
5,273,863 A   12/1993 Horn et al.
(Continued)

FOREIGN PATENT DOCUMENTS

CN    102153498 A    8/2011
DE    10201233 A1    7/2003
(Continued)

OTHER PUBLICATIONS

Re, et al., Antioxidant Activity Applying and Improved ABTS Radical Cation Decolorization Assay, Free Radical Biology & Medicine, vol. 26, pp. 1231-1237, 1999.
Zou, et al.; Fabrication of Surface-Modified CDSE Quantum Dots by Self-Assembly of a Functionalizable Comb Polymer, Polymer International, Issue 60, vol. 5, pp. 751-757, 2011.
Bagheri, et al.; Mechanisms of Antioxidant Action: Evidence for a Regenerative Cycle During the Melt Stabilisation of Polypropylene by Galvinoxyl, Polymer Degradtion and Stability, vol. 5, pp. 145-160, 1983.
Hensley et al, Nitrone-Based Free Radical Traps as Neuroprotective Agents in a Cerebral Ischaemia and Other Pathologies, Neuroprotective Agents and Cerebral Ischaemia, IRN 40, pp. 299-317, 1997.
(Continued)

*Primary Examiner* — Andrew S Rosenthal
(74) *Attorney, Agent, or Firm* — Edward L. Brant

(57) ABSTRACT

Provided are polymeric nitrones comprising polymerized units of (a) acrylates of Formula I:

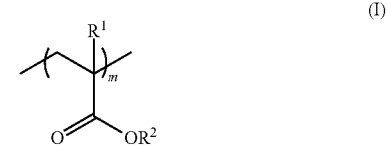

(I)

wherein $R^1$ and $R^2$ are as defined herein; and (b) nitrone-pendant esters of Formula II:

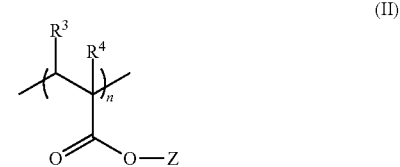

(II)

wherein $R^3$ and $R^4$ are as defined herein, and Z is a nitrone substituent of Formula III:

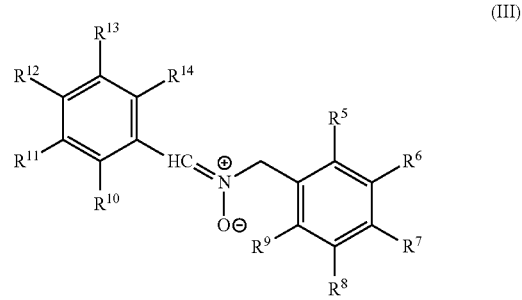

(III)

wherein $R^5$, $R^6$, $R^7$, $R^8$, $R^9$, $R^{10}$, $R^{11}$, $R^{12}$, $R^{13}$, and $R^{14}$ are as defined herein, and wherein the sum of m+n is a number from 10 to 50, and the ratio of m to n is from 1:1 to 20:1.

11 Claims, No Drawings

(51) Int. Cl.
| | |
|---|---|
| C08F 220/10 | (2006.01) |
| C08F 220/58 | (2006.01) |
| C08F 226/02 | (2006.01) |
| C09D 133/14 | (2006.01) |
| A61Q 19/08 | (2006.01) |
| A61K 9/00 | (2006.01) |
| A61K 31/785 | (2006.01) |
| C08F 220/14 | (2006.01) |
| C08F 220/28 | (2006.01) |
| C08L 33/14 | (2006.01) |

(52) U.S. Cl.
CPC ............ *A61K 31/785* (2013.01); *A61Q 19/08* (2013.01); *C08F 220/10* (2013.01); *C08F 220/14* (2013.01); *C08F 220/28* (2013.01); *C08F 220/58* (2013.01); *C08F 226/02* (2013.01); *C08L 33/14* (2013.01); *C09D 133/14* (2013.01); *A61K 2800/522* (2013.01); *A61K 2800/54* (2013.01); *A61K 2800/74* (2013.01); *C08F 2220/281* (2013.01); *C08F 2810/50* (2013.01)

(56) References Cited

U.S. PATENT DOCUMENTS

| | | | |
|---|---|---|---|
| 5,455,272 | A | 10/1995 | Janzen et al. |
| 6,002,001 | A | 12/1999 | Carney et al. |
| 7,655,251 | B2 | 2/2010 | Durand et al. |
| 9,452,118 | B2 | 9/2016 | Dhamdhere et al. |
| 9,452,119 | B2 | 9/2016 | Dhamdhere et al. |
| 9,701,625 | B2 | 7/2017 | Green et al. |
| 9,730,874 | B2 | 8/2017 | Green et al. |
| 9,796,667 | B2 | 10/2017 | Green et al. |
| 9,828,335 | B2 | 11/2017 | Green et al. |
| 2004/0241261 | A1 | 12/2004 | Prous et al. |
| 2010/0168112 | A1 | 7/2010 | Kelly et al. |
| 2012/0058088 | A1 | 3/2012 | Sardi |
| 2014/0303255 | A1 | 10/2014 | Dhamdhere et al. |
| 2018/0055749 | A1 | 3/2018 | Fhaner et al. |
| 2018/0071186 | A1 | 3/2018 | Fhaner et al. |

FOREIGN PATENT DOCUMENTS

| | | |
|---|---|---|
| EP | 1284133 | 2/2003 |
| EP | 1591104 A1 | 11/2005 |
| ES | 2316312 A1 | 4/2009 |
| IN | 1377CHE2009 | 6/2012 |
| JP | 2011251914 A | 12/2011 |
| WO | 9222290 A1 | 12/1992 |
| WO | 02065993 A2 | 8/2002 |
| WO | 2005041905 A2 | 5/2005 |
| WO | 2005087214 A1 | 9/2005 |
| WO | 2009108999 A1 | 9/2009 |
| WO | 2011130400 A1 | 10/2011 |
| WO | 2012150370 | 11/2012 |
| WO | 2012150370 A1 | 11/2012 |
| WO | 2013081778 A3 | 1/2015 |

OTHER PUBLICATIONS

Samadi, et al; Synthesis, Structure, Theoretical and Experimental In Vitro Antioxidant/Pharmacological Properties of X-Aryl, N-Alkyl Nitrones, as Potential Agents for the Treatment of Cerebral Ischemia, Bioorganic & Medicinal Chemistry 19, pp. 951-960, 2011.

Floyd, et al.; Nitrones, Their Value as Therapeutics and Probes to Understand Aging, Mechanisms of Ageing and Development, vol. 123, pp. 1021-1031, 2002.

Scott, et al.; Mechanisms of Antioxidant Action: Rubber Bound Antioxidants Based on Nitrones-1 Non-Sulphur Vulcanizates, European Polymer Journal, Volu 14, pp. 905-912, 1978.

Croitour, M D. "Nitrones Are Able to Release Nitric Oxide in Aqueous Environment Under Hydroxyl Free Radical Attack", Nitric Oxide: Biology and Chemistry, vol. 25, No. 3, pp. 309-315, 2011.

Finlayson, M. "Aging With Multiple Sclerosis", J. Neurosci Nurs. vol. 36, Issue 5, pp. 1-10, 2004.

Hill, R.; Spin Traps: The New Anti-Oxidant?; Beautymagonline (Retrieved Mar. 29, 2013), Retrieved from the Internet, <URL:http://www.beautymagonline.com/beauty-articles-4/1112-spin-traps-2>, pp. 1-3.

Perricone, N.; The Wrinkle Cure: The Formula for Stopping Time, Vintage/Ebury (A Division of Random); Illustrated Edition, pp. 182-186, Jul. 1, 2001.

Wang, M., et al; Evaluation of Resveratrol Derivatives as Potential Antioxidants and identification of a Reaction Product of Resveratrol and 2,2-Diphenyl-1-Picryhydrazyl Radical; Journal of Agricultural and Food Chemistry, vol. 47, No. 10, pp. 3974-3977, 1999.

Hung, C, et al; Biol Pharm Bull, vol. 31, Issue 5, pp. 955-962, 2009.

Fabris, S. et al; Antioxidant Properties of Resveratrol and Piceid on Lipid Peroxidation in Micelles and Monolamellar Liposomes; Biophysical Chemistry, vol. 135, pp. 76-83, 2008.

Fang, J-G, et al; Structure-Activity Relationship and Mechanism of the Tocopherol-Regenerating Activity of Resveratrol and Its Analogues; Journal of Agricultural and Food Chemistry, vol. 56, pp. 11458-11463, 2008.

Lee, Soo-Jin, et al; Resveratrol With Antioxidant Activity Inhibits Matrix Metalloproteinase Via Modulation of SIRT1 in Human Fibrosarcoma Cells; Life Sciences, vol. 88, pp. 465-472, 2011.

Kasiotis, et al; Reservatrol and Related Stilbenes: Their Anti-Aging and Anti-Angiogenic Roperties; Food and Chemical Technology, vol. 61, pp. 112-120, 2013.

Burgess Book, 2005.

Kliegel et al; Canadian Journal of Chemistry, vol. 76, Issue 7, pp. 1082-1092, 1998.

\* cited by examiner

POLYMERIC NITRONES AND THEIR USE IN PERSONAL CARE

FIELD OF THE INVENTION

This invention relates generally to compounds and compositions that are useful as antioxidants in personal care formulations. The compounds are polymeric nitrones that contain both nitrone and phenolic functionalities.

BACKGROUND

Personal care compositions are important products for most consumers. Personal care compositions contain a variety of additives that provide a wide array of benefits to the composition.

Antioxidants are among the additives commonly used in personal care compositions. Antioxidants help protect the skin from the damaging effects of free radicals caused by various environmental stresses, such as exposure to UV rays. Free radicals include, for example, singlet oxygen. Free radicals cause damage to the skin with the end result being a loss of elasticity of the skin and the appearance of wrinkles leading to premature aging of the skin.

Based on the physiological mechanism of the aging process, oxidative stress due to increased level of reactive oxygen species (ROS) especially caused by physiological stress or solar ultraviolet radiation can accelerate skin aging. There is evidence that intrinsic and extrinsic aging (i.e., photoaging) have several overlapping biochemical and molecular mechanisms. Type I collagen constitutes the major structural component of dermal connective tissue and provides dermis with tensile strength and stability. Degradation of collagen in the dermis has been reported in intrinsic aged and photoaged skin. Additionally, a major signaling pathway contributing to photoaging by ROS is the up-regulation of matrix metalloproteinase-1 (MMP-1), which leads to degradation of dermal collagen, associated with aging spots and wrinkles. Therefore, stronger antioxidants are needed as potential anti-aging ingredients to provide protection.

One such antioxidant that has been studied, as disclosed in WO 2012/150370, is resveratrol (3,5,4'-trihydroxy-trans-stilbene). Resveratrol is a naturally occurring polyphenolic compound found in the skin of grapes and other fruits. It has been investigated in the context of its potential chemopreventive properties against skin damage from UV exposure and against ROS induced damage associated with brain function, heart disease, and cancer. However, the natural abundance of resveratrol is low, and it is thus very expensive.

Consequently, there is a need to develop new antioxidant compositions for use in personal care, including compositions that mitigate degradation of collagen in skin.

STATEMENT OF INVENTION

We have now found that polymeric polyhydroxy nitrones have equivalent efficacy as radical scavengers at lower concentrations (as measured by duration of antioxidant protection), or higher efficacy (less oxidative damage and/or longer antioxidant protection) at equivalent concentrations as compared to conventional antioxidants. It has also been found that the performance of nitrones cannot be achieved by simply adding two different antioxidants, e.g., one with a phenolic functionality and another with nitrone functionality. Rather, the presence of both functionalities in the same molecule is an important aspect of their favorable performance.

Accordingly, one aspect of the invention provides an antioxidant polymeric nitrone composition comprising polymerized units of:

(a) Acrylates of Formula I:

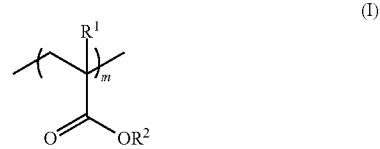

wherein $R^1$ is H or $CH_3$, and $R^2$ is $C_1$-$C_6$ alkyl, phenyl, hydroxy $C_1$-$C_6$ alkyl, dihydroxy $C_1$-$C_6$ alkyl, polyoxyalkylene, N,N-dimethylamino $C_2$-$C_6$ alkyl, N,N-diethylamino $C_2$-$C_4$ alkyl; and (b) Nitrone-Pendant Esters of Formula II:

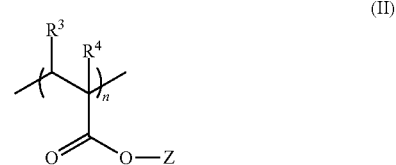

wherein $R^3$ is H or —COOH, $R^4$ is H or $CH_3$, and

Z is a nitrone substituent of Formula III:

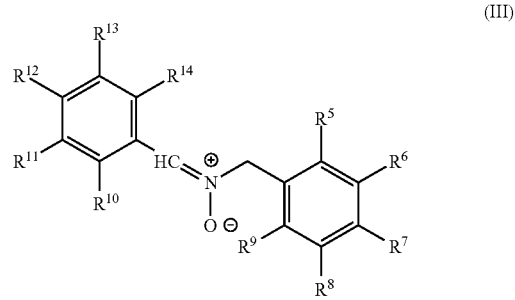

wherein $R^5$, $R^6$, $R^7$, $R^8$, and $R^9$ are independently H, —OH, $C_1$-$C_6$ alkoxy, —COOH, —COO$^-$M$^+$ or —O$^-$M$^+$, where M$^+$ is a sodium, potassium, or ammonium ion, $R^{10}$, $R^{11}$, $R^{12}$, $R^{13}$, and $R^{14}$ are independently H, —OH, $C_1$-$C_6$ alkoxy, —COOH, —COO$^-$M$^+$ or —O$^-$M$^+$, where M$^+$ is a sodium, potassium, or ammonium ion, or a substituent of Formula IV:

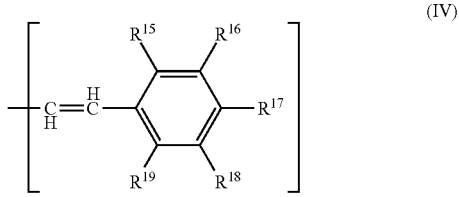

(IV)

wherein $R^{15}$, $R^{16}$, $R^{17}$, $R^{18}$, and $R^{19}$ are independently H, —OH, $C_1$-$C_6$ alkoxy, —COOH, —COO$^-$M$^+$ or —O$^-$M$^+$, where M$^+$ is a sodium, potassium, or ammonium ion;
wherein the ester of Formula II is attached to the nitrone of Formula III at either of the phenyl rings thereon, with the proviso that if $R^{10}$, $R^{11}$, $R^{12}$, $R^{13}$, or $R^{14}$ is a substituent of Formula IV, then the ester of Formula II is attached to the nitrone of Formula III at the phenyl ring opposite the ring on which the substituent of Formula IV is attached, and the proviso that not more than one of $R^{10}$, $R^{11}$, $R^{12}$, $R^{13}$, or $R^{14}$ can be a substituent of Formula IV, and the further proviso that at least two of $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, and $R^{19}$ are —OH, and wherein the sum of m+n is a number from 10 to 50, and the ratio of m to n is from 1:1 to 20:1.

Another aspect of the invention provides a personal care composition comprising (a) the antioxidant polymeric nitrone described above, and (b) a dermatologically acceptable carrier.

In another aspect, the invention provides a cosmetic method of treating skin which comprises applying to the skin a polymeric nitrone composition as described herein.

In a still further aspect, there is provided a method for inhibiting the degradation of collagen, the method comprising topically administering to skin an effective amount of an antioxidant polymeric nitrone composition as described herein.

In a yet further aspect, there is provided a method for reducing the visible signs of aging, the method comprising applying to skin in need of such treatment an antioxidant polymeric nitrone composition as described herein.

DETAILED DESCRIPTION

Unless otherwise indicated, numeric ranges, for instance as in "from 2 to 10," are inclusive of the numbers defining the range (e.g., 2 and 10). Unless otherwise indicated, ratios, percentages, parts, and the like are by weight. "Room temperature," as used in this specification, is the ambient temperature, for example, 20-25° C.

"Alkyl," as used in this specification, encompasses straight and branched chain aliphatic hydrocarbon groups having the indicated number of carbon atoms. If no number is indicated, then 1-6 alkyl carbons are contemplated. Unless otherwise indicated, the alkyl group is optionally substituted with 1, 2, or 3, preferably 1 or 2, more preferably 1, substituents that are compatible with the syntheses described herein. Such substituents include, but are not limited to, nitro, halogen, carboxylic acids (e.g., $C_0$-$C_6$—COOH), $C_2$-$C_6$ alkene, cyano, amido, and/or ester. Unless otherwise indicated, the foregoing substituent groups are not themselves further substituted.

As noted above, in one aspect the invention provides an antioxidant polymeric nitrone composition comprising polymerized units of (a) acrylates of Formula I and (b) nitrone-pendant esters of Formula II, wherein the sum of m+n is a number from 10 to 50, and the ratio of m to n is from 1:1 to 20:1. In certain preferred embodiments, the sum of m+n is a number from 10 to 35, and more preferably from 15 to 25. In certain preferred embodiments, the ratio of m to n is from 5:1 to 10:1. In certain embodiments, the polymer contains sufficient acrylate polymers to be partially water soluble. As used herein the term "partially water soluble" means that at least 0.5 weight percent of the polymeric nitrone is soluble in water at room temperature based on the total weight of the composition.

In certain embodiments at least three of $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, and $R^{19}$ are —OH.

In certain embodiments $R^{10}$, $R^{11}$, $R^{12}$, $R^{13}$, and $R^{14}$ are independently H, —OH, $C_1$-$C_6$ alkoxy, —COOH, —COO$^-$M$^+$ or —O$^-$M$^+$, where M$^+$ is a sodium, potassium, or ammonium ion. In certain of such embodiments, the nitrone of Formula III comprises one of those specified in Table 1:

TABLE 1

Specified Nitrones of Formula III

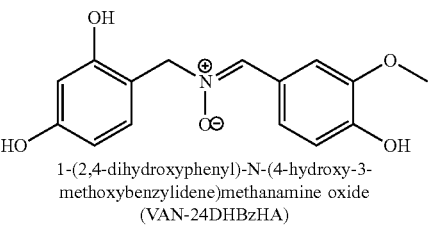

1-(2,4-dihydroxyphenyl)-N-(4-hydroxy-3-methoxybenzylidene)methanamine oxide
(VAN-24DHBzHA)

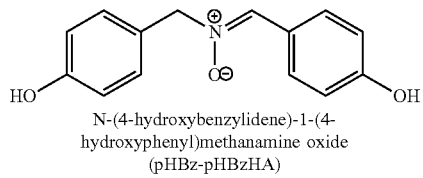

N-(4-hydroxybenzylidene)-1-(4-hydroxyphenyl)methanamine oxide
(pHBz-pHBzHA)

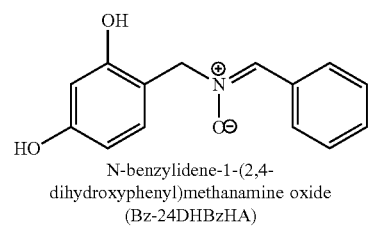

N-benzylidene-1-(2,4-dihydroxyphenyl)methanamine oxide
(Bz-24DHBzHA)

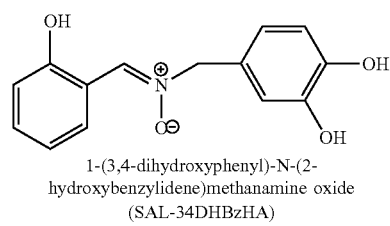

1-(3,4-dihydroxyphenyl)-N-(2-hydroxybenzylidene)methanamine oxide
(SAL-34DHBzHA)

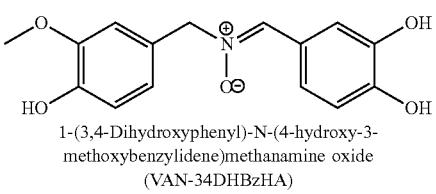

1-(3,4-Dihydroxyphenyl)-N-(4-hydroxy-3-methoxybenzylidene)methanamine oxide
(VAN-34DHBzHA)

TABLE 1-continued

Specified Nitrones of Formula III

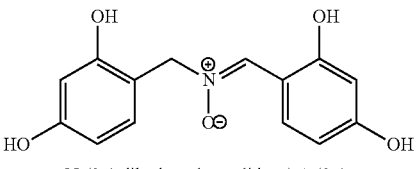

N-(2,4-dihydroxybenzylidene)-1-(2,4-
dihydroxyphenyl)methanamine oxide
(24DHBz-24DHBzHA)

In certain embodiments one of $R^{10}$, $R^{11}$, $R^{12}$, $R^{13}$, and $R^{14}$ is a substituent of Formula IV, and the ester of Formula II is attached to the nitrone of Formula III at the phenyl ring opposite the ring on which the substituent of Formula IV is attached. In certain of such embodiments, the nitrone of Formula III comprises one of those specified in Table 2:

TABLE 2

Specified Nitrones of Formula III

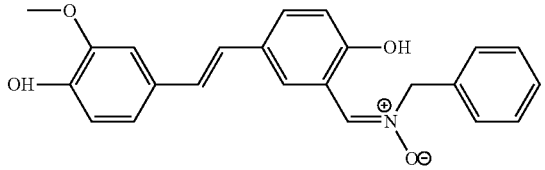 [SMILES: COc1cc(/C=C/c2ccc(O)c(/C=[N+](/[O-])Cc3ccccc3)c2)ccc1O]

N-(2-Hydroxy-5-(4-hydroxy-3-methoxystyryl)benzylidene)-
1-phenylmethanamine oxide
(Sald-BzHA)

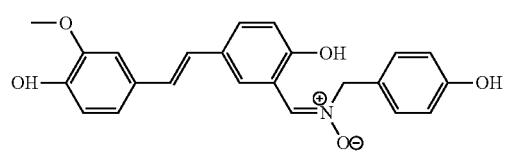 [SMILES: COc1cc(/C=C/c2ccc(O)c(/C=[N+](/[O-])Cc3ccc(O)cc3)c2)ccc1O]

N-(2-Hydroxy-5-(4-hydroxy-3-methoxystyryl)benzylidene)-1-(4-
hydroxyphenyl)methanamine oxide
(Sald-pHBzHA)

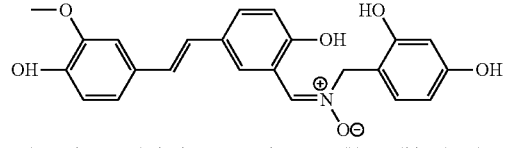 [SMILES: COc1cc(/C=C/c2ccc(O)c(/C=[N+](/[O-])Cc3ccc(O)cc3O)c2)ccc1O]

N-(2-Hydroxy-5-(4-hydroxy-3-methoxystyryl)benzylidene)-1-(2,4-
dihydroxyphenyl)methanamine oxide
(Sald-24DHBzHA)

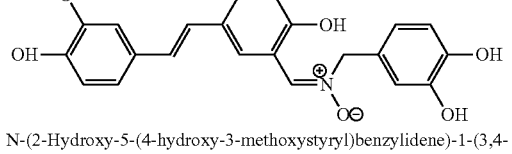

N-(2-Hydroxy-5-(4-hydroxy-3-methoxystyryl)benzylidene)-1-(3,4-
dihydroxyphenyl)methanamine oxide
(Sald-34DHBzHA)

In certain preferred embodiments, the acrylate of Formula I is:

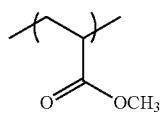

and the nitrone-pendant ester of Formula II is:

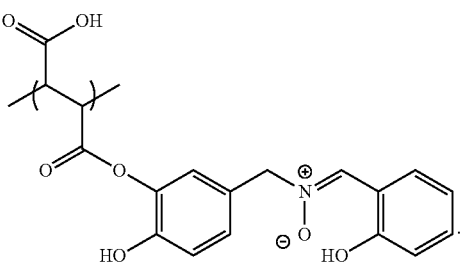

In certain preferred embodiments, the acrylate of Formula I is:

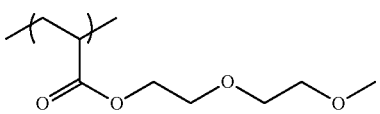

and the nitrone-pendant ester of Formula II is:

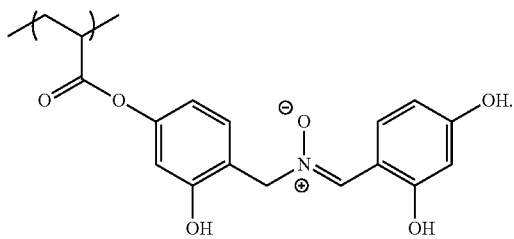

The nitrone substituents of Formula III may be readily prepared by those skilled in the art using known synthetic techniques. Certain embodiments in which none of $R^{10}$, $R^{11}$, $R^{12}$, $R^{13}$, and $R^{14}$ is a substituent of Formula IV may be prepared, for example, by the reaction of a phenyl aldehyde compound (containing one or more hydroxyl groups on the phenyl, such as 4-hydroxybenzaldehyde) with a benzylhydroxylamine compound (also containing one or more hydroxyl groups on the phenyl, such as 3,4-dihydroxybenzylhydroxylamine), followed by isolation and purification of the desired product. Certain embodiments in which one of $R^{10}$, $R^{11}$, $R^{12}$, $R^{13}$, and $R^{14}$ is a substituent of Formula IV may be prepared, for example, by the reaction of a stilbene aldehyde compound (possibly containing one or more hydroxyl groups, such as (E)-2-hydroxy-5-(4-hydroxy-3-methoxystyryl)benzaldehyde) with a benzylhydroxylamine compound (also possibly containing one or more hydroxyl groups on the phenyl, such as 3,4-dihydroxybenzylhydroxylamine), followed by isolation and purification of the desired product.

The polymeric nitrones of the present invention may be readily prepared by those skilled in the art using known synthetic techniques, for example, by bulk polymerization or emulsion polymerization. Certain embodiments in which $R^3$ and $R^4$ of the nitrone-pendant ester of Formula II are —COOH and H, respectively, can be prepared, for example, by copolymerizing an acrylate of Formula I, e.g., methyl acrylate, and maleic anhydride in ethyl acetate using 2,2'-azobisisobutyronitrile as an initiator, replacing the ethyl acetate with 1,4-dioxane, and reacting the copolymer solution with a nitrone of Formula III. Certain embodiments in which $R^3$ and $R^4$ of the nitrone-pendant ester of Formula II are both H, and the acrylate of Formula I is, for example, diethyleneglycol methyl ether acrylate, can be prepared, for example, by solution polymerization of acryloyl chloride in tetrahydrofuran using 2,2'-azobisisobutyronitrile as an initiator to obtain polyacryloyl chloride, replacing the tetrohydrofuran with 1,4-dioxane, and reacting sequentially first with diethylene glycol methyl ether and triethylamine, and then with a nitrone of Formula III and triethylamine.

In another aspect, the invention provides a personal care composition comprising (a) the antioxidant polymer nitrone compositions described herein and (b) a dermatologically acceptable carrier. A person of ordinary skill in the art can readily determine the effective amount of the inventive antioxidant polymeric nitrone that should be used in a particular composition in order to provide the benefits described herein (e.g., free radical scavenging and inhibition of collagen degradation), via a combination of general knowledge of the applicable field as well as routine experimentation where needed. By way of non-limiting example, the amount of the polymeric nitrone in the composition of the invention may be in the range of from 0.01 to 5 weight percent, preferably from 0.05 to 3 weight percent, and more preferably from 0.1 to 1 weight percent, based on the total weight of the composition.

Compositions of the invention also include a dermatologically acceptable carrier. Such material is typically characterized as a carrier or a diluent that does not cause significant irritation to the skin and does not negate the activity and properties of active agent(s) in the composition. Examples of dermatologically acceptable carriers that are useful in the invention include, without limitation, emulsions, creams, aqueous solutions, oils, ointments, pastes, gels, lotions, milks, foams, suspensions, powders, or mixtures thereof. In some embodiments, the composition contains from about 99.99 to about 50 percent by weight of the dermatologically acceptable carrier, based on the total weight of the composition.

The dermatologically acceptable carrier of the invention may also include, for instance, water, a thickener, an emollient, an emulsifier, a humectant, a surfactant, a suspending agent, a film forming agent, a foam building agent, a preservative, an antifoaming agent, UV filters, a fragrance, a lower monoalcoholic polyol, a high boiling point solvent, a propellant, a colorant, a pigment, glycerin, a mineral oil, silicone feel modifiers, triglycerides, polyolefins, waxes, preservatives, emollients, or mixtures thereof.

Other additives may be included in the compositions of the invention such as, but not limited to, abrasives, absorbents, aesthetic components such as fragrances, pigments, colorings/colorants, essential oils, skin sensates, astringents (e.g., clove oil, menthol, camphor, eucalyptus oil, eugenol, menthyl lactate, witch hazel distillate), anti-caking agents, antifoaming agents, antimicrobial agents (e.g., iodopropyl butylcarbamate), other antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), opacifying agents, pH adjusters, propellants, reducing agents, sequestrants, skin bleaching and lightening agents (e.g., hydroquinone, kojic acid, ascorbic acid, magnesium ascorbyl phosphate, ascorbyl glucosamine), skin-conditioning agents (e.g., humectants, including miscellaneous and occlusive), skin soothing and/or healing agents (e.g., panthenol and derivatives (e.g., ethyl panthenol), aloe vera, pantothenic acid and its derivatives, allantoin, bisabolol, and dipotassium glycyrrhizinate), skin treating agents, thickeners, and vitamins (e.g., Vitamin C) and derivatives thereof.

The composition of the invention may be, for example, in the form of an oil, a gel, a solid stick, a lotion, a cream, a milk, an aerosol, a spray, a foam, a mousse, an ointment or a fatty ointment or a powder.

Compositions of the invention may be used in a variety of personal care applications, such as in cosmetics and in skin care (e.g., lotions, creams, oils, topical medicines, and sunscreens).

The compositions of the invention may be manufactured by processes well known in the art, e.g., by means of conventional mixing, dissolving, granulating, emulsifying, encapsulating, entrapping or lyophilizing processes.

As noted above, compositions of the invention, containing a compound of Formula I, are highly effective as radical scavengers. They exhibit significantly better antioxidant attributes compared to previously known antioxidants for personal care applications. Furthermore it has been found that the performance of nitrones that have phenolic groups cannot be achieved by simply adding two different antioxidants, one with a phenolic functionality and another with nitrone functionality. Rather, the presence of both functionalities in the same molecule is an important aspect of their favorable performance.

The cosmetic compositions of the invention are useful for the treatment and protection of skin from free radicals caused, for instance, by exposure to ultraviolet light, such as UVA and UVB rays, as well as other harmful forms of radiation, such as long wave infrared.

Thus, for instance, the cosmetic compositions may be used in a method for inhibiting the degradation of collagen. According to such method, an effective amount of the composition may be topically administering to skin in need of such treatment.

The compositions may also be used in a method for reducing the visible signs of aging, which may result from the radical induced degradation of collagen in the skin, by applying to skin in need of such treatment the composition. Visible signs of aging may include, for instance, development of textural discontinuities such as wrinkles and coarse deep wrinkles, skin lines, crevices, bumps, large pores, or unevenness or roughness, reducing fine lines, loss of skin elasticity (loss and/or inactivation of functional skin elastin), sagging (including puffiness in the eye area and jowls), loss of skin firmness, loss of skin tightness, loss of skin recoil from deformation, discoloration (including undereye circles), blotching, sallowness, hyperpigmented skin regions such as age spots and freckles, keratoses, abnormal differentiation, hyperkeratinization, elastosis, and other histological changes in the stratum corneum, dermis, epidermis, the skin vascular system (e.g., telangiectasia or spider vessels), and underlying tissues, especially those proximate to the skin.

In practicing the methods of the invention, the cosmetic composition are generally administered topically by applying or spreading the compositions onto the skin. A person of ordinary skill in the art can readily determine the frequency with which the cosmetic compositions should be applied. The frequency may depend, for example, on the amount of sunlight that an individual is likely to encounter in a given day and/or the sensitivity of the individual to sunlight. By way of non-limiting example, administration on a frequency of at least once per day may be desirable.

Some embodiments of the invention will now be described in detail in the following Examples.

EXAMPLES

Example 1

Synthesis of Polyacrylate Polymer Substrate: Polymethyl Acrylate—Maleic Anhydride Copolymer (PMA-c-MAnh)

A 100 mL 1-neck flask was equipped with a stir bar and a 3-way stopcock. Methyl acrylate (MA, 9.56 grams, 0.111 moles) and maleic anhydride (MAnh, 3.3 grams, 0.0337 moles) were dissolved in the flask in 50 mL of ethyl acetate. The flask was purged with nitrogen, sealed, and cooled in a dry ice/isopropanol bath. After freezing, the flask was placed under vacuum, re-sealed, and then allowed to warm to room temperature. This process was repeated 4 additional times. The purged monomer solution was combined with 0.46 grams of 2,2'-azobis(2-methylpropionitrile) (AIBN). The flask was again sealed, and then heated to 50° C. for 18 hours. Gel permeation chromatography showed the presence of a trace of MAnh to be present. The polymer solution volume obtained was 63.8 mL, which had a MA content of 0.111 moles (1.74 mmoles/mL) and a MAnh content of 0.0337 moles (0.528 mmoles/ML).

Synthesis of Polyacrylate Polymer with Pendant Nitrone: Polymethyl Acrylate—Maleic Anhydride—Nitrone 1-(3,4-dihydroxyphenyl)-N-(2-hydroxybenzylidene)methanamine Oxide Copolymer (PMA-c-MAnh-C-SAL-34DHBzHAA)

A 1.3 mL aliquot of polymer substrate PMA-c-MAnh as prepared above was transferred to a small vial. This aliquot contained 0.528 mmoles of MAnh. The ethyl acetate was removed under a stream of dry nitrogen. The residue was combined with 5.0 mL of dry 1,4-dioxane and a solution of 0.1369 grams (0.528 mmoles) of the nitrone dihydroxyphenyl)-N-(2-hydroxybenzylidene)methanamine oxide (SAL-34DHBzHA) dissolved in an additional 10 mL of 1,4-dioxane. The vial was sealed and placed into an oven maintained at 75° C. After 24 hours, the vial was removed from the oven, and was allowed to cool to room temperature. Gel permeation chromatography analysis of the reaction mixture indicated that there was no free nitrone remaining. The solvent was removed from the reaction mixture by rotary evaporation to give 0.767 grams of product as a dark red oil. $^1$H-NMR analysis indicated that the ratio of maleic acid to nitrone was about 5 to 1 based on the ratio of methyl ester to aryl hydrogens.

Example 2

Synthesis of Polyacrylate Polymer Substrate: Polydiethyleneglycol Methyl Ether Acrylate—Acryloyl Chloride Copolymer (PAC-c-DEGMEA)

Freshly distilled acryloyl chloride (AC, 11.4 grams, 0.126 moles) was mixed with 25 mL of inhibitor-free anhydrous tetrahydrofuran (THF) in a flask. The flask was purged with nitrogen, sealed, and cooled in a dry ice/isopropanol bath. After freezing, the flask was placed under vacuum, re-sealed, and then allowed to warm to room temperature. This process was repeated 4 additional times. The purged monomer solution was combined with 0.48 grams of 2,2'-azobis(2-methylpropionitrile) (AIBN), and the mixture was heated at 50° C. overnight to result in a solution containing 3.5M polyacryloyl chloride (PAC) in THF (3.5 mmoles/mL).

The polyacryloyl chloride—diethyleneglycol methyl ether acrylate copolymer was prepared according to the procedure described in W. Zou, et al., Polymer International, 60(5), 751 (2011). A 1.0 mL aliquot of the above PAC solution in THF was transferred to a small vial, and the THF was removed under a stream of dry nitrogen. Dry 1,4-dioxane (5.0 mL) was then added to the solution, followed by 0.245 grams (2.04 mmoles) of diethylene glycol methyl ether. The vial was sealed and placed into an oven maintained at 75° C. After 24 hours, the vial was removed from the oven, and was allowed to cool to room temperature. The PAC-c-DEGMEA solution contained about 2.04 mmoles of diethyleneglycol methyl ether acrylate and 1.46 mmoles about 1.46 mmoles of acryloyl chloride.

Synthesis of Polyacrylate Polymer with Pendant Nitrone: Polydiethyleneglycol Methyl Ether Acrylate—Nitrone 1-(2,4-dihydroxyphenyl)-N-(2,4-dihydroxybenzylidene)methanamine Oxide Copolymer (PDEGMEA-c-24DHBz-24DHBzHAA)

A 1.0 mL aliquot of polymer substrate PAC-c-DEGMEA as prepared above was transferred to a small vial. This aliquot contained 1.46 mmoles of acryloyl chloride. The THF was removed under a stream of dry nitrogen. The residue was combined with 5.0 mL of 1,4-dioxane and a solution of 0.413 grams (1.46 mmoles) of nitrone dihydroxyphenyl)-N-(2,4-dihydroxybenzylidene)methanamine oxide (24DHBz-24DHBzHA) dissolved in an additional 10 mL of 1,4-dioxane. The vial was sealed and placed into an oven maintained at 75° C. The reaction mixture was checked after a short time at 75° C., and it was found that not all of the nitrone had dissolved. DMSO (1.5 mL) was added to the mixture, and a clear solution resulted. The vial was returned to the oven. After 24 hours, the vial was removed from the oven, and was allowed to cool to room temperature. The dioxane solvent was removed from the reaction mixture under a stream of dry nitrogen. The residual viscous DMSO solution was mixed with about 15 mL of water, resulting in a 2-phase liquid mixture: an upper, clear dark amber aqueous mixture; and a lower, viscous yellow-brown oil phase. The aqueous layer was decanted from the oil, and the oil was washed with another 15 mL portion of water. After again decanting off the water phase, the oil was dissolved in about 15 mL of THF. This solution was dried over anhydrous magnesium sulfate, and the solvent was removed under a stream of dry nitrogen. The residual oil was dried in a vacuum oven at 65° C. for about 2 hours to give 0.696 grams of product as a red viscous oil.

Example 3

Antioxidant Potential

Antioxidant potential is evaluated using the Oxygen Radical Absorbance Capacity (ORAC) protocol. ORAC is a chemical in-vitro method based on the hydrogen atom transfer (HAT) mechanism (see N. Re et al., *Free Radical*

*Biology & Medicine*, 26 (9/10), 1231 (1997)). ORAC measures antioxidant inhibition of peroxyl radical induced oxidations and thus reflects classical radical chain breaking antioxidant activity by H atom transfer. In this assay, the peroxyl radical reacts with a fluorescent probe to form a non-fluorescent product. This is quantitated using a fluorescence measurement. Antioxidant capacity is determined by decreased rate and amount of product formed over time. This assay depends upon the free radical damage to the fluorescent probe resulting in the change in its fluorescence intensity. The change of fluorescence intensity is an indicator of the degree of free radical damage. In the presence of an antioxidant, the inhibition of free radical damage is reflected in higher fluorescence intensity and can be measured as antioxidant capacity against the free radicals. The uniqueness of ORAC assay is that the reaction is driven to completion. This allows calculation of the area under the curve (AUC) and gives an absolute quantitation of antioxidancy as opposed to relative measurements in many other assays.

As noted, the longer it takes to observe a decrease in fluorescence, the higher the antioxidant (AO) potential. From the AUC for a given antioxidant, the AUC for blank is subtracted to give its ORAC value. The concentration of AO needed to give the same AUC values as Trolox is calculated and used to represent the Trolox equivalent AO Capacity (TEAC). Trolox is ((±)-6-Hydroxy-2,5,7,8-tetramethylchromane-2-carboxylic acid, CAS #53188-07-1), and is used as an internal control.

The ORAC test is conducted in the stilbene-pendant nitrone compounds of Table 1 above (inventive compounds) as well as to Vitamin C, Vitamin E, and the following comparative compounds:

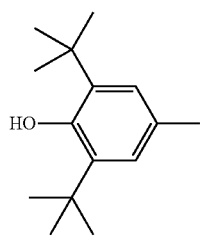 [SMILES: Cc1cc(C(C)(C)C)c(O)c(C(C)(C)C)c1]

Butylated hydroxytoluene (BHT)

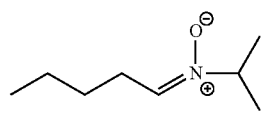

(Z)—N-pentylidenepropan-2-amine oxide (VAL-IPHA)

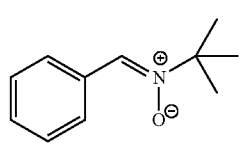

2-Phenyl-N-tert-butylnitrone (PBN)

The inventive stilbene-pendant nitrones in the ORAC test solutions were at a concentration of 100 micromolar, while the concentrations of Trolox, Vitamin C, Vitamin E, BHT, PBN+BHT, and VAL-IPHA were at 100 micromolar. The TEAC values calculated from the ORAC values are listed the Table 2.

TABLE 2

| TEAC Values | |
|---|---|
| ANTIOXIDANT COMPOUND | TEAC |
| Vitamin C (comparative) | 0.76 |
| Vitamin E (comparative) | 0.13 |
| BHT (comparative) | 0.11-0.21 |
| PBN + BHT (comparative) | 0.24 |
| VAL-IPHA (comparative) | 0.18 |
| PMA-c-MAnh-C-SAL-34DHBzHAA (inventive Example 1) | 2.23 |
| PDEGMEA-c-24DHBz-24DHBzHAA (inventive Example 2) | 1.99 |

Surprisingly, it is found that the polymeric nitrones of the invention displayed significantly higher ORAC values compared to the known antioxidants Vitamin E or C. It is also evident that the TEAC values of phenolic AOs such as BHT, a non-aromatic nitrone such as VAL-IPHA, or an aromatic nitrone such as PBN are not very high compared to the TEAC values of the polymeric nitrones invention. The TEAC value for a physical blend of an aromatic nitrone and a phenolic AO (PBN+BHT) is relatively small also.

What is claimed is:

1. A polymeric nitrone comprising polymerized units of:
   (a) acrylates of Formula I:

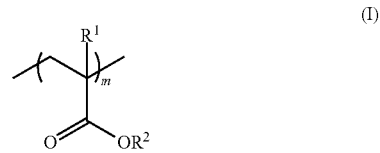

wherein
   $R^1$ is H or $CH_3$; and
   $R^2$ is $C_1$-$C_6$ alkyl, phenyl, hydroxy $C_1$-$C_6$ alkyl, dihydroxy $C_1$-$C_6$ alkyl, polyoxyalkylene, N,N-dimethylamino $C_2$-$C_6$ alkyl, N,N-diethylamino $C_2$-$C_4$ alkyl; and
   (b) nitrone-pendant esters of Formula II:

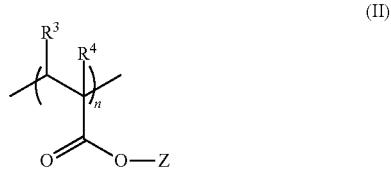

wherein
   $R^3$ is H or —COOH;
   $R^4$ is H or $CH_3$, and

Z is a nitrone substituent of Formula III:

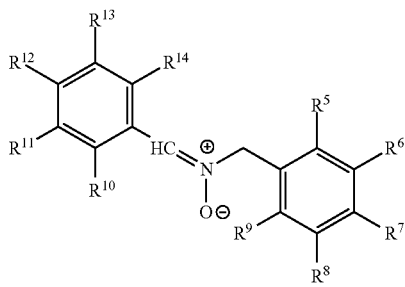
(III)

wherein
$R^5$, $R^6$, $R^7$, $R^8$, and $R^9$ are independently H, —OH, $C_1$-$C_6$ alkoxy, —COOH, —COO$^-$M$^+$ or —O$^-$M$^+$, where M$^+$ is a sodium, potassium, or ammonium ion; and $R^{10}$, $R^{11}$, $R^{12}$, $R^{13}$, and $R^{14}$ are independently H, —OH, $C_1$-$C_6$ alkoxy, —COOH, —COO$^-$M$^+$ or —O$^-$M$^+$, where M$^+$ is a sodium, potassium, or ammonium ion, or a substituent of Formula IV:

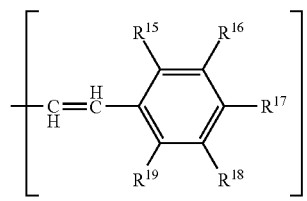
(IV)

wherein
$R^{15}$, $R^{16}$, $R^{17}$, $R^{18}$, and $R^{19}$ are independently H, —OH, $C_1$-$C_6$ alkoxy, —COOH, —COO$^-$M$^+$ or —O$^-$M$^+$, where M$^+$ is a sodium, potassium, or ammonium ion, wherein the ester of Formula II is attached to the nitrone of Formula III at either of the phenyl rings thereon, wherein one of $R^{10}$, $R^{11}$, $R^{12}$, $R^{13}$, or $R^{14}$ is a substituent of Formula IV, wherein the ester of Formula II is attached to the nitrone of Formula III at the phenyl ring opposite the ring on which the substituent of Formula IV is attached, and the proviso that not more than one of $R^{10}$, $R^{11}$, $R^{12}$, $R^{13}$ or $R^{14}$ can be a substituent of Formula IV, and the further proviso that at least two of $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, and $R^{19}$ are —OH; and wherein the sum of m+n is a number from 10 to 50, and the ratio of m to n is from 1:1 to 20:1.

2. The polymeric nitrone of claim 1 wherein at least three of $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, and $R^{19}$ are —OH.

3. The polymeric nitrone of claim 1 wherein
the acrylate of Formula I is:

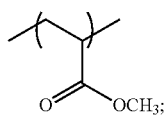

and
the nitrone-pendant ester of Formula II is:

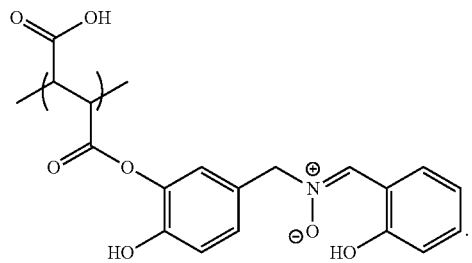

4. The polymeric nitrone of claim 1 wherein:
the acrylate of Formula I is:

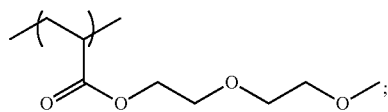

and
the nitrone-pendant ester of Formula II is:

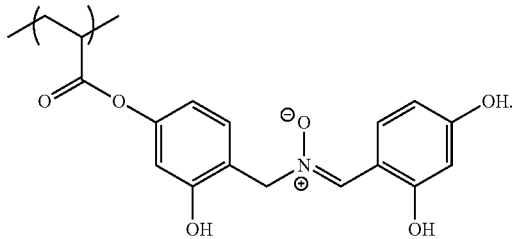

5. A personal care composition comprising:
(1) a polymeric nitrone comprising polymerized units of:
 (a) acrylates of Formula I:

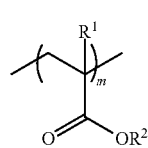
(I)

wherein
$R^1$ is H or $CH_3$; and
$R^2$ is $C_1$-$C_6$ alkyl, phenyl, hydroxy $C_1$-$C_6$ alkyl, dihydroxy $C_1$-$C_6$ alkyl, polyoxyalkylene, N,N-dimethylamino $C_2$-$C_6$ alkyl, N,N-diethylamino $C_2$-$C_4$ alkyl; and (b) nitrone-pendant esters of Formula II:

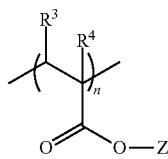
(II)

wherein
R³ is H or —COOH;
R⁴ is H or CH₃, and
Z is a nitrone substituent of Formula III:

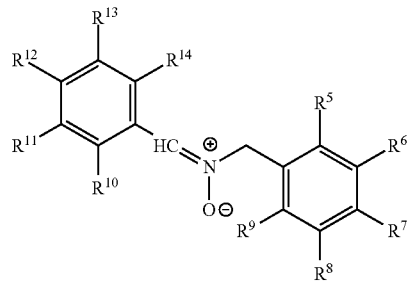
(III)

wherein
R⁵, R⁶, R⁷, R⁸, and R⁹ are independently H, —OH, $C_1$-$C_6$ alkoxy, —COOH, —COO⁻M⁺ or —O⁻M⁺, where M⁺ is a sodium, potassium, or ammonium ion; and
R¹⁰, R¹¹, R¹², R¹³, and R¹⁴ are independently H, —OH, $C_1$-$C_6$ alkoxy, —COOH, —COO⁻M⁺ or —O⁻M⁺, where M⁺ is a sodium, potassium, or ammonium ion, or a substituent of Formula IV:

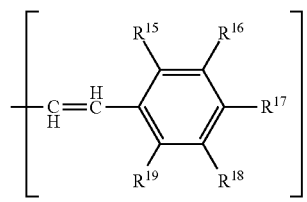
(IV)

wherein
R¹⁵, R¹⁶, R¹⁷, R¹⁸, and R¹⁹ are independently H, —OH, $C_1$-$C_6$ alkoxy, —COOH, —COO⁻M⁺ or —O⁻M⁺, where M⁺ is a sodium, potassium, or ammonium ion,
wherein the ester of Formula II is attached to the nitrone of Formula III at either of the phenyl rings thereon, wherein one of R¹⁰, R¹¹, R¹², R¹³, or R¹⁴ is a substituent of Formula IV, wherein the ester of Formula II is attached to the nitrone of Formula III at the phenyl ring opposite the ring on which the substituent of Formula IV is attached, and the proviso that not more than one of R¹⁰, R¹¹, R¹², R¹³, or R¹⁴ can be a substituent of Formula IV, and the further proviso that at least two of R⁵, R⁶, R⁷, R⁸, R⁹, R¹⁰, R¹¹, R¹², R¹³, R¹⁴, R¹⁵, R¹⁶, R¹⁷, R¹⁸, and R¹⁹ are —OH; and
wherein the sum of m+n is a number from 10 to 50, and the ratio of m to n is from 1:1 to 20:1; and
(2) a dermatologically acceptable carrier.

6. The personal care composition of claim 5 wherein at least three of R⁵, R⁶, R⁷, R⁸, R⁹, R¹⁰, R¹¹, R¹², R¹³, R¹⁴, R¹⁵, R¹⁶, R¹⁷, R¹⁸, and R¹⁹ are —OH.

7. The personal care composition of claim 5 wherein the acrylate of Formula I is:

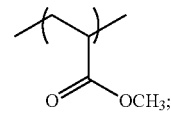

and
the nitrone-pendant ester of Formula II is:

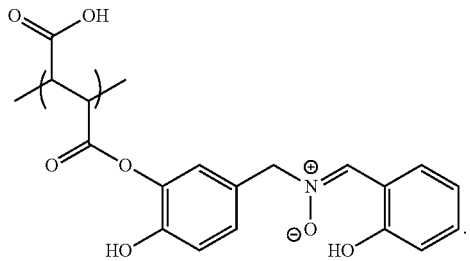

8. The personal care composition of claim 5 wherein the acrylate of Formula I is:

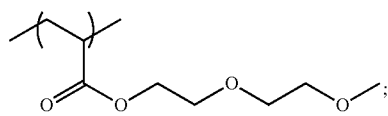

and
the nitrone-pendant ester of Formula II is:

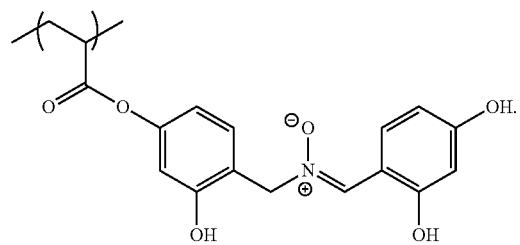

9. A cosmetic method of treating skin comprising applying to the skin the composition of claim 6.

10. A method for inhibiting the degradation of collagen in skin, the method comprising: topically administering to the skin an effective amount of the composition of claim 5.

11. A method for reducing the visible signs of aging, the method comprising: applying to skin in need of such treatment the composition of claim 5.

* * * * *